(12) United States Patent
Derksen et al.

(10) Patent No.: US 12,402,837 B2
(45) Date of Patent: Sep. 2, 2025

(54) TENSOR AMPLIFICATION-BASED DATA PROCESSING

(71) Applicant: The Regents of the University of Michigan, Ann Arbor, MI (US)

(72) Inventors: Hendrikus Derksen, Dexter, MI (US); Neriman Tokcan, Somerville, MA (US); Kayvan Najarian, Northville, MI (US); Jonathan Gryak, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 1241 days.

(21) Appl. No.: 17/167,140

(22) Filed: Feb. 4, 2021

(65) Prior Publication Data

US 2021/0338171 A1 Nov. 4, 2021

Related U.S. Application Data

(60) Provisional application No. 62/970,653, filed on Feb. 5, 2020.

(51) Int. Cl.
*G06F 17/00* (2019.01)
*A61B 5/00* (2006.01)
(Continued)

(52) U.S. Cl.
CPC ............ *A61B 5/7264* (2013.01); *A61B 5/318* (2021.01); *G06F 16/908* (2019.01); *G06F 17/40* (2013.01);
(Continued)

(58) Field of Classification Search
CPC ..... A61B 5/7264; A61B 5/318; A61B 5/1455; A61B 5/7203; A61B 5/7267;
(Continued)

(56) References Cited

U.S. PATENT DOCUMENTS 11,355,240 B2 * 6/2022 Hirsch ................... G16H 50/20
11,829,867 B2 * 11/2023 Iwakura ................. G06N 5/022
(Continued)

OTHER PUBLICATIONS

Xuyu Wang, Chao Yang, and Shiwen Mao. TensorBeat: Tensor Decomposition for Monitoring Multiperson Breathing Beats with Commodity WiFi. ACM Trans. Intell. Syst. Technol. 9, 1, Article 8, 27 pages. <https://doi.org/10.1145/3078855>, Sep. 2017.*
(Continued)

*Primary Examiner* — Greta L Robinson
(74) *Attorney, Agent, or Firm* — Lempia Summerfield Katz LLC

(57) ABSTRACT

A method of generating an assessment of medical condition for a patient includes obtaining a patient data tensor indicative of a plurality of tests conducted on the patient, obtaining a set of tensor factors, each tensor factor of the set of tensor factors being indicative of a decomposition of training tensor data for the plurality of tests, the decomposition amplifying low rank structure of the training tensor data, determining a patient tensor factor for the patient based on the obtained patient data tensor and the obtained set of tensor factors, applying the determined patient tensor factor to a classifier such that the determined further tensor factor establishes a feature vector for the patient, the classifier being configured to process the feature vector to generate the assessment, and providing output data indicative of the assessment.

20 Claims, 7 Drawing Sheets

(51) Int. Cl.

| | |
|---|---|
| *A61B 5/318* | (2021.01) |
| *G06F 16/908* | (2019.01) |
| *G06F 17/40* | (2006.01) |
| *G06N 20/00* | (2019.01) |
| *G16H 50/20* | (2018.01) |
| *G16H 50/30* | (2018.01) |
| *G16H 50/70* | (2018.01) |

(52) U.S. Cl.
CPC ............. *G06N 20/00* (2019.01); *G16H 50/20* (2018.01); *G16H 50/30* (2018.01); *G16H 50/70* (2018.01)

(58) Field of Classification Search
CPC ....... G06F 16/908; G06F 17/40; G06N 20/00; G16H 50/20; G16H 50/30; G16H 50/70
See application file for complete search history.

(56) References Cited

U.S. PATENT DOCUMENTS

| | | | | |
|---|---|---|---|---|
| 2008/0063264 | A1* | 3/2008 | Porikli | G06V 10/50 382/224 |
| 2011/0119209 | A1* | 5/2011 | Kirshenbaum | G06N 5/02 706/12 |
| 2020/0005929 | A1* | 1/2020 | Tablan | G16H 50/20 |

OTHER PUBLICATIONS

L.-H. Lim and P. Comon, Multiarray signal processing: tensor decomposition meets compressed sensing, Comptes Rendus Mecanique 338 (2010), 311-320.
R. Bro, Multi-way Analysis in the Food Industry: Models, Algorithms and Applications, Ph. D. thesis, University of Amsterdam, 1998. Available at: http://www.models.kv1.dk/research/theses.
Z. Wen, W. Yin and Y. Zhang, Solving low-rank factorization model for matrix completion by a nonlinear successive over-relaxation algorithm, Rice CAAM Tech Report 10-07, University of Rice, 2010.
A. Anandkumar, R. Ge, D. Hsu, S. Kakade and M. Telgarsky, Tensor decompositions for learning latent variable models, J. of Machine Learning Research 15 (2014), 2773-2832.
A. Cichocki, Era of Big Data Processing: A new approach via tensor networks and tensor decompositions, Preprint 2014, arXiv:1403.2048.
A. Rajwade, A. Rangarajan and A. Banerjee, Image Denoising using Higher Order Singular Value Decomposition, IEEE Trans. on Pattern Analysis and Machine Intelligence (PAMI) 35 (2013), 849-862.
A. Rajwade, A. Rangarajan and A. Banerjee, Using the Higher Order Singular Value Decomposition (HOSVD) for Video Denoising, Energy Minimization Methods in Computer Vision and Pattern Recognition (EMMCVPR), Springer, NCS 6819, 2011, 344-354.
A. Ramlatchan et al., A survey of matrix completion methods for recommendation systems, Big Data Mining and Analytics, 1 (2018) No. 4, 308-323.
A. Özdemir, M. A. Iwen and S. Aviyente, "A multiscale approach for tensor denoising" 2016 IEEE Statistical Signal Processing Workshop (SSP), 2016, pp. 1-5, doi: 10.1109/SSP.2016.7551841.
B. Mishra, G. Meyer, F. Bach and R. Sepulchre, Low-rank optimization with trace norm penalty, Preprint, 2011, http://arxiv.org/abs/1112.2318.
B. Mitchell and D. S. Burdick, Slowly converging PARAFAC sequences: Swamps and two-factor degeneracies, J. Chemometrics 8 (1994), 155-168.
B. Recht and C. Ré, Parallel stochastic gradient algorithms for large-scale matrix completion, Math. Programming Computation 5 (2013), 201-226.
B. Recht, M. Fazel and P. Parillo, Guaranteed minimum rank solutions of linear matrix equations via nuclear norm minimization, SIAM Review 52 (2010), No. 3, 471-501.
B. W. Bader, T. G. Kolda and others, MATLAB Tensor Toolbox, Version [Version], available online at https://www.tensortoolbox.org, 2021.
C. J. Hillar and L.-H. Lim, Most tensor problems are NP-hard, Journal of the ACM 60 (2013), No. 6, Art. 45.
C. Navasca, L. de Lathauwer and S. Kinderman, Swamp reducing technique for tensor decompositions, in: Proceedings of the 16th European Signal Processing Conference (EUSIPCO 2008), Lausanne, 2008.
D. L. Donoho, Compressed Sensing, IEEE Trans. on Information Theory 52 (2006), 1289-1306.
D. Nion and L. De Lathauwer, An enhanced line search scheme for complex-valued tensor decompositions. Application in DS-CDMA, Signal Process. 88 (2008), 749-755.
E. J. Candès and B. Recht, Exact matrix completion via convex optimization, Found. of Comput. Math. 9, 2009, 717-772.
E. J. Candès and Y. Plan, Matrix completion with noise, Proceedings of the IEEE 98, 2010, 925-936.
E. J. Candès, J. K. Romberg and T. Tao, Stable signal recovery from incomplete and inaccurate measurements, Comm. on Pure and Appl. Math. 59 (2006), 1207-1223.
F. L. Hitchcock, Multiple invariants and generalized rank of a p-way matrix or tensor, J. Math. Phys. 7, No. 1, 39-79.
F. L. Hitchcock, The expression of a tensor or a polyadic as a sum of products, J. Math. Phys. 6 (1927), No. 1, 164-189.
G. Tomasi, Practical and Computational Aspects in Chemometric Data Analysis, Ph. D. thesis, Deparment of Food Science, The Royal Veterinary and Agricultural University, Frederiksberg, Denmark, 2006. Available at http://www.models.life.ku.dk/research/thesis.
H. Derksen, A general theory of singular values with applications to signal denoising, SIAM Journal on Appl. Alg. and Geom., 2017, arXiv:1705.10881.
H. Derksen, On the nuclear norm and the singular value decomposition of tensors, Found. Comput. Math. 16 (2016), No. 3, 779-811.
H. Weyl, The Classical Groups. Their Invariants and Representations, Princeton University Press, 1939.
J. D. Carroll and J. Chang, Analysis of individual differences in multidimensional scaling via an N-way generalization of "Eckart-Young" decomposition, Psychometrika 35 (1970), 283-319.
J. Hastad, Tensor rank is NP-complete, J. Algorithms 11 (1990), No. 4, 644-654.
J. Jiang, H. Wu, Y. Li and R. Yu, Three-way data resolution by alternating slice-wise diagonalization (ASD) method, J. CHemometrics 14 (2000), 15-36.
J. M. Landsberg, Tensors: Geometry and Applications, Graduate Studies in Mathematics 128, American Mathematical Society, Providence, RI, 2012.
K. C. Toh and S. Yun, An accelerated proximal gradient algorithm for nuclear norm regularized linear least squares problems, Pacific Journal of Optimization 6 (2010), 615-640.
M. Rajih and P. Comon, Enhanced line search: A novel method to accelerate PARAFAC, in: EUSIPCO-05: Proceedings of the 13th European Signal Processing Conference, 2005.
N. Srebro, J. Rennie and T. Jaakkola, Maximum margin matrix factorization, in: Advances in Neural Information Processing Systems (NIPS) 17 (2005).
OEIS Foundation Inc. (2019), The On-Line Encyclopedia of Integer Sequences, http://oeis.org/A002831.
P. A. Wang and C. J. Lu, Tensor decomposition via simultaneous power iteration, Proceedings of the 34th International Conference on Machine Learning, PMLR 70:3665-3673, 2017.
P. Jain, R. Meka and I. S. Dhillon, Guaranteed rank minimization via singular value projection, in: Advances in Neural Information processing Systems (NIPS) 22 (2010), 937-945.
P. Paatero, Construction and analysis of degenerate PARAFAC models, J. Chemometrics 14 (2000), 285-299.
R. A. Harshman, Foundations of the parafac procedure: models and conditions for an "explanatory" multimodal factor analysis, UCLA working papers in Phonetics 16 (1970), 1-84.
R. Brauer, On algebras which are connected with the semisimple continuous groups, Annals of Mathematics 38 (1937), No. 4, 857-872.

(56) References Cited

OTHER PUBLICATIONS

R. H. Keshavan, A. Montanari and S. Oh, Matrix completion from a few entries, IEEE Trans. on Information Theory 56 (2010), 2980-2998.

R. Keshavan and S. Oh, Optspace: A gradient descent algorithm on the Grassmann manifold for matrix completion, preprint 2009, http://arxiv.org/abs/0910.5260.

R. Mazumder, T. Hastie and R. Tibshirani, Spectral regularization algorithms for learning large incomplete matrices, J. of Machine Learning Research 11 (2010), 2287-2322.

R. Schatten, A Theory of Cross-Spaces, Princeton University Press, Princeton, NJ, 1950.

S. Friedland, L.-H. Lim, Nuclear norm of higher-order tensors, Mathematics of Computation 87 (2018), No. 311, 1255-1281.

S. Ji and J. Ye, An accelerated gradient method for trace norm minimization, in: Proceedings of the 26th International Conference on Machine Learning (ICML), 2009, 457-464.

S. Ma, D. Goldfarb and L. Chen, Fixed point and Bregman iterative methods for matrix rank minimization, Mathematical Programming 128 (2011), 321-353.

T. G. Kolda and B. W. Bader, Tensor decompositions and applications, SIAM review 51 (2009), No. 3, 455-500.

V. L. Popov and E. B. Vinberg, "Invariant theory" in: Encyclopaedia of Mathematical Sciences, vol. 55, A. Parshin and I. R. Shafarevich, eds., Springer-Verlag, Berlin, 1994.

W. Hu, Y. Xie, W. Zhang, L. Zhu, Y. Qu and Y. Tan, Image denoising via nonlocally sparse coding and tensor decomposition, Proceedings of International Conference on Internet Multimedia Computing and Service (ICMCS '14), 2014.

W. S. Rayens and B. C. Mitchell, Two-factor degeneracies and a stabilization of PARAFAC, Chemometrics and Intelligent Laboratory Systems 38 (1997), 173-181.

Y. Liu, D. Sun and K.-C. Toh, An implementable proximal point algorithmic framework for nuclear norm minimization, Mathematical Programming 133 (2012), 399-436.

Y. Wang, H.-Y. Tung, A. J. Smola and A. Anandkumar, Fast and guaranteed tensor decomposition via sketching, Advances in Neural Information Processing Systems 28 (NIPS 2015).

Z. Lu and Y. Zhang, Penalty decomposition methods for rank minimization, preprint, 2010, http://arxiv.org/abs/0910.5260.

Z. Weng, M.-J. Lai, Z. Lu, W. Fan, H. Davulcu and J. Ye, Orthogonal rank-one matrix pursuit for low rank matrix completion, Preprint 2014, http://arxiv.org/abs/1404.1377.

Goodman et al., "Symmetry, Representations, and Invariants", Graduate Texts in Mathematics, Chapter 10, p. 428, Fig. 10.2, 2009, Springer.

J.-F. Cai, E. J. Candes and Z. Shen, "A Singular Value Thresholding Algorithm for Matrix Completion", SIAM J. on Optimization 20, 1956-1982, (2010).

Smilde et al., "Multi-way Analysis with Applications in the Chemical Sciences", Chapter 6, pp. 116-118 "Initializing PARAFAC-ALS", 2004, Wiley.

\* cited by examiner

TENSOR AMPLIFICATION-BASED DATA PROCESSING

CROSS-REFERENCE TO RELATED APPLICATION

This application claims the benefit of U.S. provisional application entitled "Tensor Amplification-Based Data Processing," filed Feb. 5, 2020, and assigned Ser. No. 62/970,653, the entire disclosure of which is hereby expressly incorporated by reference.

STATEMENT REGARDING FEDERALLY SPONSORED RESEARCH OR DEVELOPMENT

This invention was made with government support under Contract No. W81XWH-17-2-0012 awarded by the Army Medical Research and Development Command, and Contract No. U.S. Pat. No. 1,837,985 awarded by the National Science Foundation. The government has certain rights in the invention.

BACKGROUND OF THE DISCLOSURE

Field of the Disclosure

The disclosure relates generally to medical condition detection and other data processing involving data structures with high dimensionality.

Brief Description of Related Technology

The amount of accessible data is ever increasing in quantity and variety. One of the biggest big data challenges is the analysis of multi-modal data with intrinsically high dimensionality. Previously used matrix-based representations of data and related analysis methods are incompatible with multi-modal data.

Tensors, or multi-way arrays, often provide a natural and compact representation for such massive multidimensional data. Tensor-based methods have been employed for dimensionality reduction, de-noising, completing missing data, and for identifying latent features and instances that are salient to a machine learning problem.

Unfortunately, the complexity of processing of such tensors and other structured data sets has led to techniques that involve flattening the data. But flattening the data undesirably ignores the multi-modal structure of the data. Efforts to retain the multi-modal structure of the data have done so at the expense of a tremendous amount of training data and time-consuming training processes.

Tensor-related processing presents a host of other challenges. For instance, when working in high dimensional spaces, new computational problems arise because of the exponential growth in memory and time requirements. This challenge is referred to as the curse of dimensionality.

Canonical polyadic (CP) decompositions have been developed to deal with structured high dimensional data sets. CP decompositions are based on a generalization of the notion of the rank of a matrix to higher order tensors. Unfortunately, CP decompositions are not always numerically stable or unique. This aspect has created significant challenges in using CP decompositions in Big Data applications. For instance, iterative procedures for the CP decomposition (such as alternating least squares, or ALS) may output a different tensor decomposition every time the procedure is run. Such performance renders CP decomposition unsuitable for sensitive applications, such as those presented in medicine.

SUMMARY OF THE DISCLOSURE

In accordance with one aspect of the disclosure, a method of generating an assessment of medical condition for a patient includes obtaining, by a processor, a patient data tensor indicative of a plurality of tests conducted on the patient, obtaining, by the processor, a set of tensor factors, each tensor factor of the set of tensor factors being indicative of a decomposition of training tensor data for the plurality of tests, the decomposition amplifying low rank structure of the training tensor data, determining, by the processor, a patient tensor factor for the patient based on the obtained patient data tensor and the obtained set of tensor factors, applying, by the processor, the determined patient tensor factor to a classifier such that the determined further tensor factor establishes a feature vector for the patient, the classifier being configured to process the feature vector to generate the assessment, and providing, by the processor, output data indicative of the assessment.

In accordance with another aspect of the disclosure, a method of generating an assessment of medical condition for a patient includes obtaining, by a processor, tensor data including one or more patient-based tensors for patient data indicative of a plurality of tests conducted on the patient and first and second class tensors for first and second patient classes with and without the medical condition, respectively, adjusting, by the processor, dimensionality of either the one or more patient-based tensors or the first and second class tensors via a tensor decomposition so that the one or more patient-based tensors or the first and second class tensors have a same dimensionality, the tensor decomposition generating a set of tensor factors that amplify low rank structure, computing, by the processor, first and second similarity scores for first and second tensor pairings of the one or more patient-based tensors relative to the first and second patient classes, respectively, selecting, by the processor, the first patient class or the second patient class for the assessment based on the computed first and second similarity scores, and providing, by the processor, output data indicative of the assessment.

In accordance with yet another aspect of the disclosure, a method of de-noising tensor data includes obtaining, by a processor, the tensor data, estimating, by the processor, a noise level of the tensor data using tensor amplification-based dimension reduction, implementing, by the processor, a decomposition by iteratively amplifying low rank structure of the tensor data while an error term of the decomposition is greater than the estimated noise level, and providing, by the processor, tensor factors of the decomposition when the error term is equal to or less than the estimated noise level, or a de-noised version of the tensor data based on the tensor factors.

In connection with any one of the aforementioned aspects, the methods and systems described herein may alternatively or additionally include or involve any combination of one or more of the following aspects or features. The set of tensor factors includes a tensor factor indicative of a correlation of the decomposition to multiple predetermined values of a noise level parameter. The set of tensor factors includes a tensor factor indicative of a correlation of the decomposition to timing windows for the plurality of tests. Determining the patient tensor factor includes solving a least squares problem to minimize a difference between the patient data tensor and a tensor product of the obtained tensor factors and the patient tensor factor. The method further includes forming the feature vector for the patient by combining the determined patient tensor factor with electronic health record data for the patient. The obtained set of tensor factors is indicative of training data processed via a procedure in which the training data is clustered in accordance with presence of the medical condition. The plurality of tests includes an electrocardiogram (ECG) test, a blood pressure test, and a photoplethysmography (PPG) test conducted during a time period window. The low rank structure includes a plurality of rank 1 tensors. Adjusting the dimensionality includes replacing a tensor factor generated via the tensor decomposition with a matrix that minimizes a distance between tensors for which the first and second similarity scores are computed. Obtaining the tensor data includes stacking the patient data onto the first and second class tensors to create first and second patient-based tensors. Computing the first and second similarity scores further includes determining a normalized inner product of tensors for which the first and second similarity scores are computed. Computing the first and second similarity scores further includes implementing a CP decomposition procedure on tensors for which the first and second similarity scores are computed. Selecting the first patient class or the second patient class includes determining which of the first patient class and the second patient class has a higher similarity score. Implementing the decomposition includes implementing a tensor amplification-based tensor decomposition. Estimating the noise level using tensor amplification-based dimension reduction includes generating a set of tensor factors, each tensor factor of the set of tensor factors being indicative of a decomposition of the tensor data. The tensor data is indicative of physiological data.

BRIEF DESCRIPTION OF THE DRAWING FIGURES

For a more complete understanding of the disclosure, reference should be made to the following detailed description and accompanying drawing figures, in which like reference numerals identify like elements in the figures.

Figure 1:
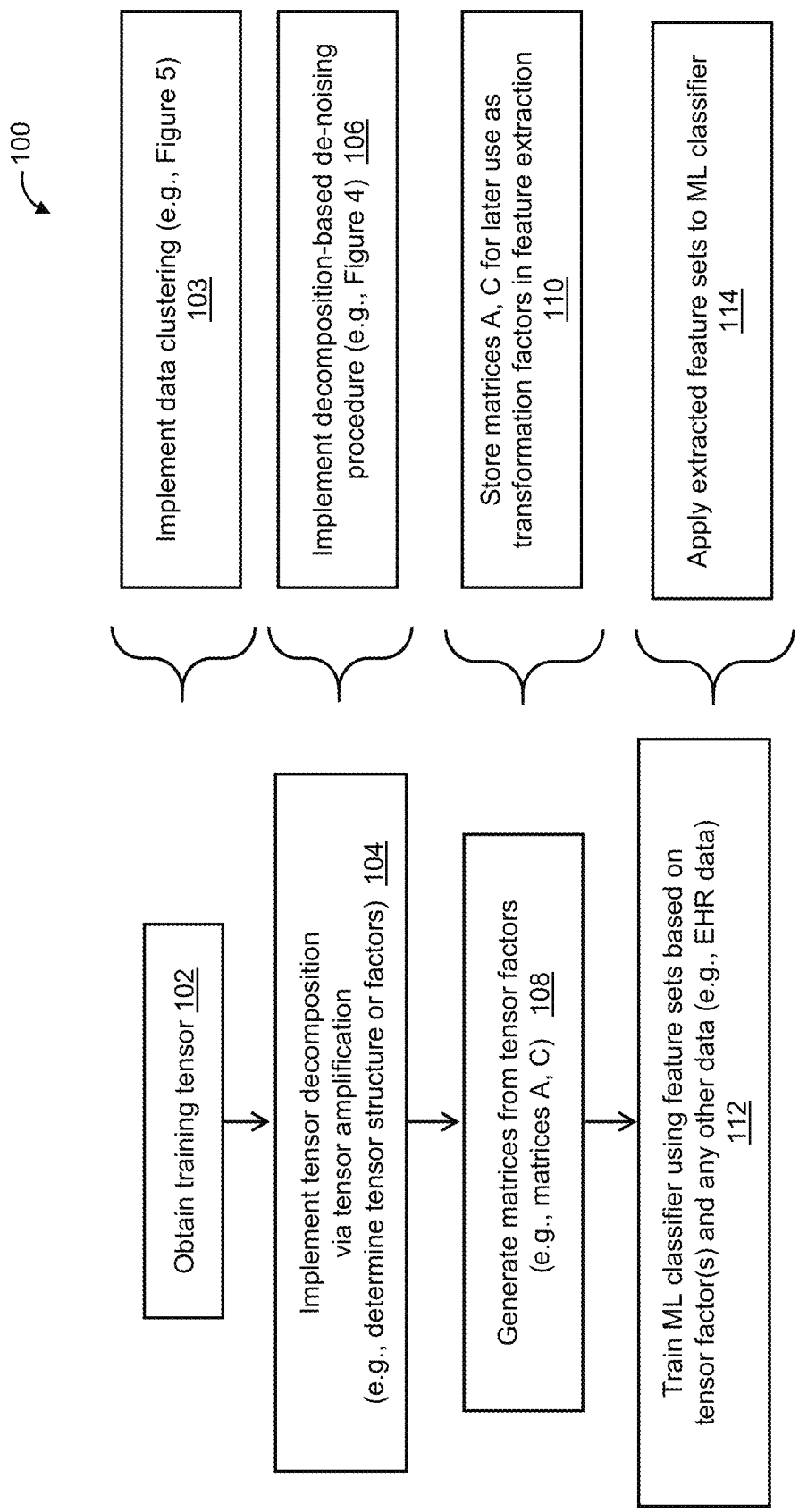
FIG. 1 depicts a flow diagram of a method of generating tensor factor data with reduced dimensionality via tensor amplification-based decomposition and training a machine learning classifier with the tensor factor data in accordance with one example.

The embodiments of the disclosed systems and methods may assume various forms. Specific embodiments are illustrated in the drawing and hereafter described with the understanding that the disclosure is intended to be illustrative. The disclosure is not intended to limit the invention to the specific embodiments described and illustrated herein.

DETAILED DESCRIPTION OF THE DISCLOSURE

Methods and systems of tensor data processing are described. The data processing of the disclosed methods and systems is based on tensor amplification techniques. The tensor amplification of the techniques is directed to amplifying low rank structure of the tensor. The tensor amplification may thus retain or incorporate the structure of the tensor, rather than flatten the tensor. The amplification of the low rank structure is enabled via algebraic computation methods described herein.

The tensor amplification-based processing of the disclosed methods and systems may be applied in a number of contexts. In some cases, tensor data indicative of a plurality of tests (e.g., physiological tests) may be processed to provide a medical condition assessment. The tensor data may be processed in preparation for application to a classifier configured to provide the assessment. For instance, the tensor amplification-based processing may be used to provide a reduced feature set to the classifier. In other cases, the tensor data is processed to directly provide the assessment based on a tensor similarity analysis. The disclosed methods and systems may thus support the integration of multimodal data for monitoring and decision support. The tensor data may alternatively or additionally be processed in accordance with the tensor amplification-based techniques for de-noising. In some cases, the de-noising is implemented in preparation for medical condition assessment. The tensor de-noising may be implemented for other purposes or in other contexts.

In some aspects, the tensor amplification-based decomposition of the disclosed methods and systems is related nuclear decompositions. The tensor amplification-based decomposition is numerically stable. The tensor amplification-based decomposition is capable of dealing with large data sets efficiently by replacing the nuclear norm (and its dual norm, the spectral norm) by norms that are computed more effectively.

In some of the examples described herein, the tensor amplification-based techniques of the disclosed methods and systems are applied to a highly complex and high-denominational problem in medicine—the early detection of sepsis. As one of the most critical conditions in medicine, sepsis is characterized by the large size and heterogeneity of the data used in its diagnosis. Multiple physiological signals, e.g. Electrocardiogram (ECG), Photoplethysmogram (PPG), Body Temperature (BT) and Arterial Blood Pressure (ABP) are useful parts of diagnosis, while all types of blood culture tests and molecular assays provide useful data about the occurrence and severity of sepsis. While each of these measurements is important for the detection of sepsis, the most characteristic feature of sepsis may be the time and structural relations across these different sources of data. For instance, while elevated heart rate might be a sign of a wide spectrum of diseases, if it is associated with high temperature and a positive blood culture test for some bacterial infection, the likelihood of sepsis as the main diagnosis significantly increases. While that pattern may be observed by a clinician, much more complex structural patterns may arise across these measurements, thereby providing more quantitative and predictive assessment of sepsis in early stages. Further complicating data-based assessment efforts, sepsis is merely a representative of many such diseases and conditions in medicine, such as Multi-Organ Dysfunction Syndrome (MODS) and Acute Respiratory Distress Syndrome (ARDS). Use of the structural patterns across the collected data may provide effective assessments for such complex medical conditions.

Although described in connection with a number of examples involving tensor data generated in connection with postoperative care for cardiac patients, the nature of the tensor data may vary widely. For instance, the tensor data may additionally or alternatively include image data from one or more imaging modalities. In cases involving medical condition assessments, the nature of the medical condition(s) may also vary from the examples shown and described herein. For instance, the disclosed methods and systems may be used for de-noising, dimensionality reduction, classification, and other data processing in connection with a wide variety of non-medical data types, including, for instance, psychometric data, chemometric data, signal processing data, and computer vision data, and in a wide variety of fields, including, for instance, compressive and medical imaging, computational biology, analog-to-information conversion, geophysics, astronomy, system identification, communication, audio and speech processing, remote sensing, and robotics.

The tensor amplification-based decomposition aspects of the disclosed methods and systems are now introduced. For each tensor T, in $\mathbb{R}^{p_1 \times p_2 \times \cdots \times p_d}$, viewed as a multi-linear function, the following operation is defined to amplify the low rank structure of the tensor.

$$\Phi(T) = \iiint T(v^{(1)}, \ldots, v^{(d)})^3 v^{(1)} \otimes v^{(2)} \otimes \ldots \otimes v^{(d)}$$

where each vector $v^{(i)}$ is integrated over the unit sphere in $\mathbb{R}^{p_i}$.

For instance, if we have an order 3 tensor $T \otimes \mathbb{R}^{p \times q \times r}$ then we integrate $v^{(1)}$, $v^{(2)}$, $v^{(3)}$ over unit spheres in $\mathbb{R}^p$, $\mathbb{R}^q$, $\mathbb{R}^r$ respectively. Using methods from invariant theory and representation theory, the integrals in may be computed efficiently.

The operation is related to spectral norm approximations because of the following $$\text{relation} - \|T\|_{\sigma,4} = \sqrt[5]{\langle \Phi(T), T \rangle},$$

where $\|T\|_{\sigma,4}$ approximates the spectral norm $\|T\|_\sigma$.

A tensor decomposition procedure, such as the example set forth below, finds a convex decomposition, where E is an error term and ε is a noise level.

$$T = \sum_{i=1}^{s} v_i^{(1)} \otimes \ldots \otimes v_i^{(d)} + E \text{ with } \|E\| \leq \varepsilon.$$

An example procedure for amplification of a tensor T is set forth below.

```
FUNCTION tensor_amplification (T,k)
    S = T
    FOR i = 1, ... , k
        S = φ(S)
        S = S/||S||
    END FOR
        RETURN S
END FUNCTION
```

After amplification, the tensor is then decomposed by using successive rank 1 approximations. In some cases, a preliminary rank 1 approximation is determined in part by choosing the maximum spectral norm out of all matrix slices of the tensor T, after which this approximation is used to initialize an alternating least squares (ALS) procedure, which gives a rank 1 approximation for T with high fit.

An example tensor decomposition procedure is set forth below.

```
FUNCTION decompose (T,ε,k)
    E = T
    s = 0
    WHILE ||E|| > ε DO
        s = s + 1
        U = tensor_amplification (E,k)
        Approximate U with unit rank 1 tensor v_s = v_s^(1) ⊗ v_2^(2) ⊗ ...
            ⊗ v_s^(d)
        Choose λ_1, ... , λ_s with ||E|| minimal, where E = T -
            (λ_1 v_1 + ... + λ_s v_s)
    END WHILE
    return decomposition T = λ_s v_s + ... + λ_s v_s + E
END FUNCTION
```

In Line 7 of the procedure, the parameter U may be close to a rank 1 tensor. A rank 1 approximation of the parameter U may be found via, e.g., a fast converging ALS algorithm or applying principal component analysis (PCA) to a flattened tensor. In Line 8 of the procedure, a least squares linear regression may be computed because s is typically small. One advantage of this example tensor decomposition procedure is that few iterations are involved in the amplification. The procedure is also useful as a global method that will not get stuck in local minima.

The tensor amplification of the example decomposition procedure shown above may be used in connection with tensor de-noising. As described herein, a tensor may be de-noised by (1) estimating the noise level, e.g., via tensor-based dimension reduction, and (2) decomposing the tensor, e.g., using the example decomposition procedure shown above. The following de-noised version of a tensor T is then provided.

$$\hat{T} = \sum_{i=1}^{r} \lambda_i (v_i^{(1)} \otimes v_i^{(2)} \otimes \ldots \otimes v_i^{(d)}).$$

In one set of comparison tests, such amplification-based de-noising yielded better results (i.e., a higher signal-to-noise ratio) than methods based on ALS and higher order single value decomposition (HOSVD).

The tensor amplification-based decomposition may also be used in classification scenarios. In one scenario, an assessment of a set of data for a patient involves selecting a cohort to which the patient data belongs. For example, one cohort p1 corresponds with healthy patients, and another cohort p2 corresponds with a certain medical condition. For each individual (i.e., the patient and the individuals in the cohorts), the data is structured as q×r data structure (e.g., q different features measured at r different stages or times). The data structures of the healthy patients A1, A2, etc. are stacked as a tensor T1. The data structures of the unhealthy patients are stacked to form a tensor T2. The new patient that needs to be diagnosed or otherwise classified has a matrix or other data structure A.

As described below, the classification may be made based on a tensor similarity score computation. For example, in some cases, the matrix A is then stacked on top of tensors T1 and T2. The new patient is then classified according to which tensor is perturbed the least. In that case, the new patient is classified as healthy (or not having the medical condition) if the following expression applies- $$\|\tilde{T}_1\|_*-\|T_1\|_*<\|\tilde{T}_2\|_*-\|T_2\|_*.$$

In other cases, the similarity score may be computed between a tensor for the new patient and the tensors T1 and T2. In either case, the tensor amplification-based decomposition may be used to support the similarity score computation by adjusting the dimensionality of the tensors being compared. The dimensionality adjustment allows the tensors to have the same dimensionality, thereby allowing an inner product-based computation for the similarity score. In either approach, one or more of the tensors may be de-noised as described herein prior to, or in conjunction with, the comparison.

Still other classification scenarios may be supported by the tensor amplification-based decomposition of the disclosed methods and systems. As described below, the decomposition may be used to support feature reduction for a machine learning-based classifier. The feature reduction and underlying decomposition are useful in several ways. For instance, the feature reduction improves the performance of the classifier by simplifying the training thereof. Additionally, the decomposition yields tensor factors that may be used as transformation factors for operation on the incoming tensor to be classified. The transformation factors may be used to generate a feature vector for the incoming tensor to be provided to the classifier. These and other aspects of this use of the tensor amplification-based decomposition of the disclosed methods and systems are described below in connection with a sepsis example involving approximately 1000 initial patient data features from a variety of tests and other sources, such as demographics, clinical data, physiological signals, lab results, and medications.

FIG. 1 depicts a method 100 directed to training a machine learning classifier in accordance with one example. The method 100 may be implemented by any one or more of the systems or processors described herein, and/or another system or processor. The method 100 uses tensor amplification-based decomposition to reduce the number of features used to train the classifier.

In some cases, the classifier is trained to generate an assessment of medical condition. The assessment may be a binary assessment, such as a positive or negative assessment of whether the patient has the medical condition. Non-binary or other assessments may be generated. For instance, the medical condition assessment may distinguish between a healthy condition, a first unhealthy condition, and a second unhealthy condition.

The method 100 may begin, in an act 102, with one or more acts directed to obtaining a training tensor. For example, a memory in which data indicative of the training tensor is stored may be accessed. Alternatively or additionally, the training tensor data may be received via one or more data communications. The manner in which the training tensor is obtained may vary. The dimensionality, nature, and other characteristics of the training tensor data may also vary. For instance, the training tensor data may be indicative of medical information (e.g., physiological signals and/or other data) or non-medical information.

In some cases, obtaining the training tensor includes or involves implementing a data clustering step or procedure. An example involving data clustering is described and shown in connection with FIG. 5. Additional or alternative data clustering or other processing may be implemented on raw or other data obtained for the training tensor.

In an act 104, a tensor amplification-based decomposition of the training tensor is implemented. The tensor amplification-based decomposition may be configured as described above. For instance, the tensor amplification and other aspects of the decomposition may include or involve execution of a procedure as described herein. The procedure determines the structure of the tensor and, in so doing, determines a number of factors. In some cases, the act 102 includes decomposition-based de-noising of the training tensor in an act 106. For instance, the de-noising may include the method shown and described in connection with FIG. 4.

The method 100 may include generation in an act 108 of a number of matrices from the tensor factors. The tensor factors may be grouped to form respective matrices. In one example, the decomposition results in four sets of tensor factors (e.g., $a_i$, $b_i$, $c_i$, $d_i$), with each tensor factor being a vector. The decomposition is thus represented as follows:

$$T=\Sigma_{i=1}^r a_i \otimes b_i \otimes c_i \otimes d_i.$$

The vectors $a_1, a_2, \ldots, a_r$ are grouped together to generate a matrix A. Similar matrices (e.g., B, C, D) may be generated from the other sets of tensor factors. The matrices may thus be also referred to herein as tensor factors. Additional or alternative tensor factors may be used in other cases.

In one medical example, the tensor factors A and C express the correlation of the components in the tensor decomposition to the different choices of delta and to different sampling windows for physiological signal data, respectively. The tensor factor B expresses how each component in the tensor decomposition correlates to the features. The tensor factor D expresses how each component correlates to the different patients in the training cohort. Further details regarding the tensor factors and other aspects of the medical example are provided below in connection with FIGS. 5 and 6.

The act 108 may include an act 110 in which one or more of the matrices are stored in a data store or other memory for later use as transformation factors. In the medical example, the factors A and C are stored, and then later used to compute a feature vector for each patient. The transformation factors may be used to extract a feature vector from patient data, including the patient data used for training the classifier. An example involving extracting the features from new patient data is described in connection with FIG. 2. For example, the matrices B and D may be discarded.

The method 100 includes an act 112 in which a machine learning classifier is trained. The classifier may be trained with the tensor factors or matrices generated as a result of the decomposition. In some cases, the tensor factors may be combined with other data (e.g., electronic health record data) to form a training feature set. In the example shown, the act 112 includes an act 114 in which the transformation factors (e.g., the matrices A and C) are used to extract features from each set of patient data in the training set. The extracted features for each training patient data set are then applied to the classifier for training.

Figure 2:
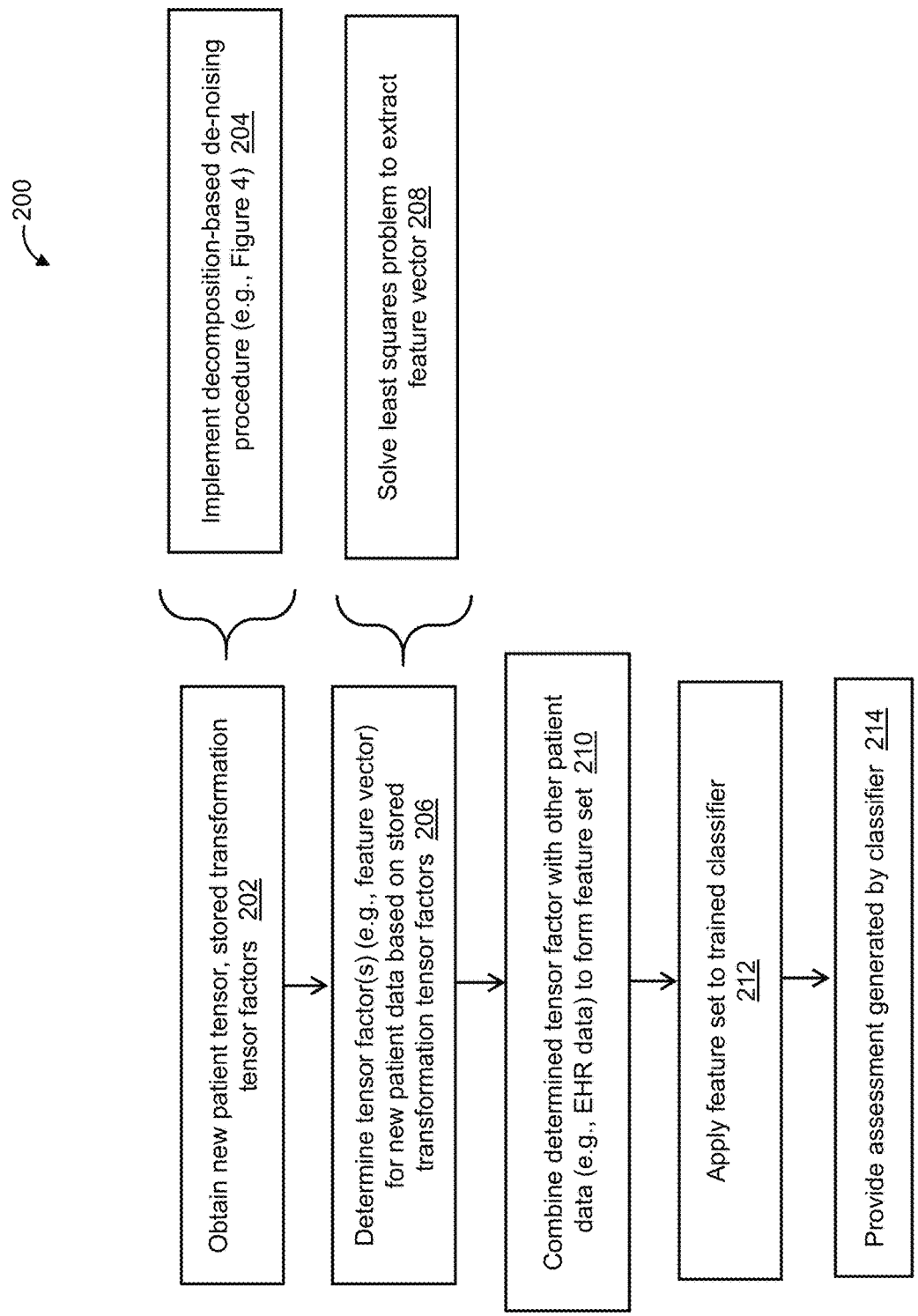
FIG. 2 depicts a flow diagram of a method of generating an assessment of medical condition for a patient in accordance with one example in which tensor amplification-based decomposition of a patient data tensor is used to apply patient feature data with reduced dimensionality to a classifier configured in accordance with the training method of FIG. 1.

FIG. 2 depicts a method 200 of generating an assessment of medical condition for a patient in accordance with one example. The method 100 may be implemented by any one or more of the systems or processors described herein, and/or another system or processor. The method 200 uses the classifier training in accordance with the method 100 of FIG. 1. As mentioned previously, the assessment may be a binary assessment, such as a positive or negative assessment of whether the patient has the medical condition, or a non-binary assessment.

The method 200 may begin, in an act 202, in which a patient data tensor indicative of a plurality of tests conducted on the patient is obtained. The manner in which the patient data tensor is obtained may vary. For instance, data clustering and/or other processing of the data underlying the patient data tensor may or may not be implemented. The dimensionality and other aspects of the patient data tensor may also vary. For instance, the number of tests may vary. In some cases, the tests include a number of physiological tests. The results of each physiological test may be sampled in a sampling or other time window. In the examples described below, the tests include an electrocardiogram (ECG) test, a blood pressure test, and a photoplethysmography (PPG) test. The patient data tensor may include data other than test result data. For instance, EHR, medication, demographic, and/or other types of data may be included.

The patient data tensor may be de-noised in an act 204. In some cases, the de-noising may include or involve implementing a decomposition-based de-noising procedure. Examples of such procedures are described herein in connection with FIG. 4. Other decomposition-based de-noising procedures may be used, including, for instance, CP-based decomposition procedures. Still other types of de-noising may be implemented.

In the example of FIG. 2, the act 202 also includes obtaining a set of tensor factors. Each tensor factor is indicative of a decomposition of training tensor data for the plurality of tests. The decomposition may include or involve the method of FIG. 1, or another decomposition procedure or method. As described herein, the decomposition amplifies low rank structure of the training tensor data. The low rank structure may correspond with a sum of a small number of rank 1 tensors of high magnitude (e.g., as measured by the norm of the factor). A large number of rank 1 tensors of small magnitude will mostly consist of noise.

The obtained set of tensor factors may be indicative of the training data processed via a procedure in which the training data is clustered. For instance, the training data may be clustered before decomposition in the same manner that the patient tensor data is clustered. In some cases, the training data is clustered in accordance with presence of the medical condition. Alternative or additional processing of the training data may be implemented. For instance, the tensor decomposition may be implemented to generate a respective reduced-size tensor for both positive and negative cases of the medical condition, and the reduced-size tensors for the positive and negative cases may then be stacked.

The tensor factors may be configured as transformation factors to be used to determine a feature vector for the new patient data. For instance, one of the transformation factors may be indicative of a correlation of the decomposition to multiple predetermined values of a noise level parameter (delta), to be distinguished from the noise level of the convex decomposition described above. The features extracted depend on the noise level parameter (delta). For example, for the Heart-Rate-Variability (HRV) taut string data discussed below, features are derived from a taut string method for denoising that depends on the noise level parameter (delta). Another transformation factor may be indicative of a correlation of the decomposition to timing windows for the plurality of tests.

In an act 206, a patient tensor factor is determined for the patient based on the obtained patient data tensor and the obtained set of tensor factors (e.g., the transformation factors). The patient tensor factor may be configured as, or otherwise include or involve, a feature vector. In some cases, the patient tensor factor is determined by solving a least squares problem in an act 208 to minimize a difference between the patient data tensor and a tensor product of the obtained tensor factors and the patient tensor factor. An example of the determination of the act 206 is provided below in connection with FIGS. 5 and 6.

The method 200 may also include an act 210 in which a feature set is formed for the patient by combining the determined patient tensor factor with electronic health record data and/or other for the patient.

The tensor factor for the patient (or the feature set including the tensor factor) is then applied in an act 212 to a trained classifier, such as the classifier trained in accordance with the method 100 of FIG. 1. The classifier may have been trained using training data based on or otherwise related to the obtained tensor factors. For instance, the classifier is configured via training using features obtained by using the tensor factors (e.g., the tensor factors A and C) from the decomposition. The determined further tensor factor thus establishes a feature vector for the patient. The classifier is configured to process the feature vector to generate the assessment (e.g., the medical condition assessment). Output data indicative of the assessment generated by the classifier in this example may then be provided in an act 214. For example, the assessment output data may be provided via a display and/or via a data transmission. Other types of output data or data provision may be used.

The order in which the acts of the method 200 are implemented may differ from the example shown in FIG. 2, and/or the method 200 may include additional, fewer or alternative acts. For instance, the act 202 may be implemented via two separate and distinct acts (or sets of acts) related to the new patient tensor and the transformation tensor factors.

Figure 3:
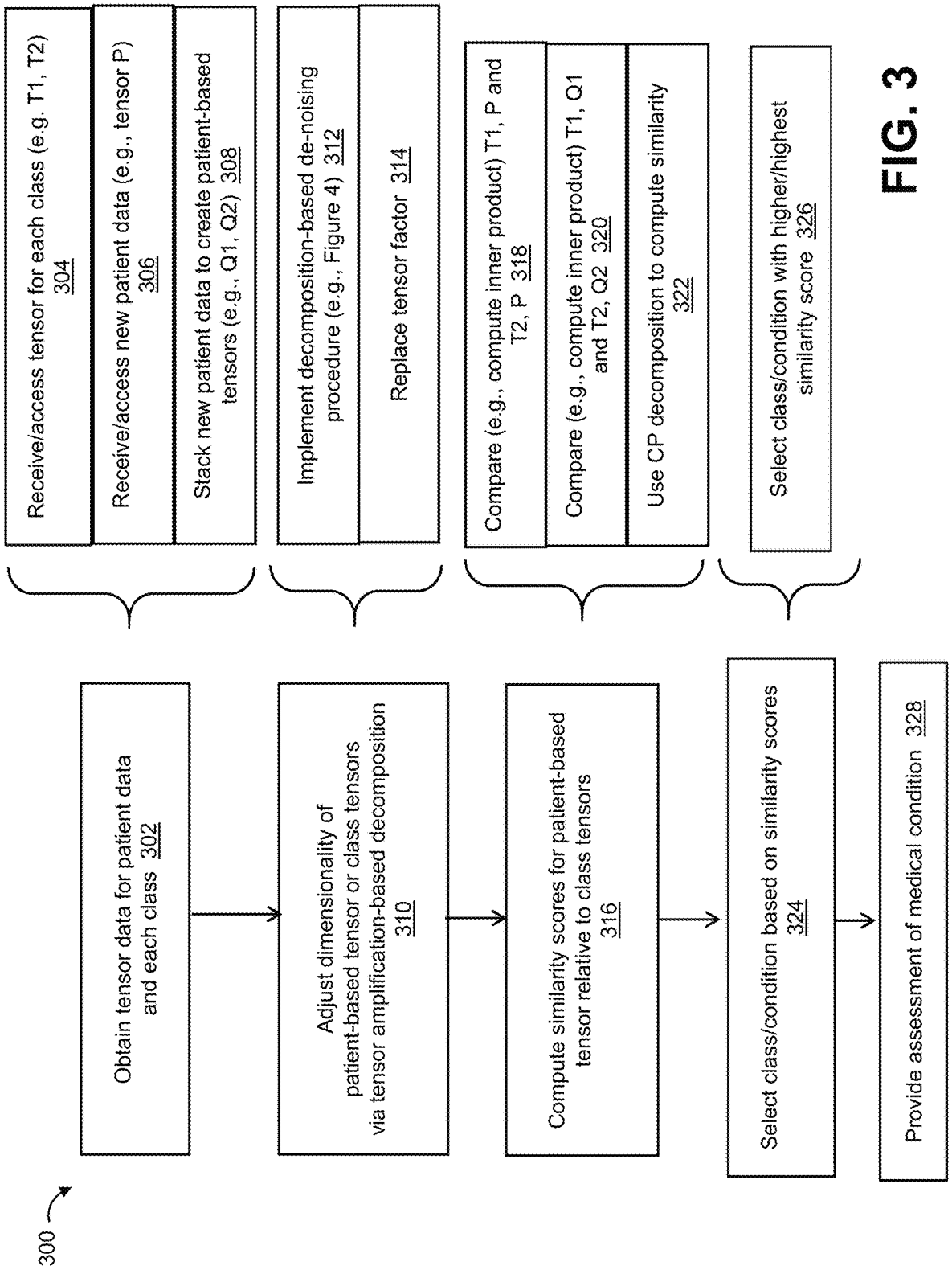
FIG. 3 depicts a flow diagram of a method of generating an assessment of medical condition for a patient based on computation of tensor similarity scores using tensor amplification-based decomposition to generate tensor data having the same dimensionality in accordance with one example.

FIG. 3 depicts a method 300 of generating an assessment of medical condition for a patient in accordance with another example. The method 300 may be implemented by any one or more of the systems or processors described herein, and/or another system or processor. The method 300 is similar to the above-described assessment methods in the sense that the assessment is based upon a tensor amplification-based decomposition of patient tensor data. However, the method 300 differs from the above-described methods in that a machine learning model or other classifier is not relied upon for the assessment. Instead, the method 300 relies upon a tensor decomposition-based similarity analysis to generate the assessment. The assessment may again be a binary assessment, such as a positive or negative assessment of whether the patient has the medical condition, or a non-binary assessment.

The method 300 may begin, in an act 302, in which tensor data is obtained for a new patient and for first and second patient classes with and without the medical condition, respectively. The tensor data thus includes one or more patient-based tensors (P) for the patient data. The patient-based tensor(s) P may be indicative of a plurality of tests conducted on the patient. The tensor data also includes first and second class tensors T1, T2 for the first and second patient classes with and without the medical condition, respectively. The first and second class tensors T1, T2 are also indicative of the results of the plurality of tests on the first and second patient classes. The nature of the tests, and the tensor data, may thus be similar to the other assessment methods described herein.

The tensor data may be obtained in various ways. The act 302 may include an act 304 in which a tensor is received, accessed, or otherwise obtained for each class (e.g., tensors T1, T2). The act 302 may additionally include an act 306 in which new patient data is received, accessed, or otherwise obtained.

The new patient data may be obtained as a tensor (e.g., tensor P), or as data to be subsequently arranged as a tensor. The tensor arrangement may include the new patient data alone (e.g., the tensor P), or the new patient data in combination with the class tensor data. For example, in some cases, the new patient data is stacked in an act 308 on the class tensors to create first and second patient-based tensors (e.g., Q1, Q2). In either case, the dimensionality of the tensors being compared (e.g., either P vs. T1 and T2, or Q1 vs. T1 and Q2 vs. T2) involves only one of the dimensions.

In an act 310, the dimensionality of either the one or more patient-based tensors (e.g., the tensor P or the tensors Q1, Q2) or the first and second class tensors (e.g., the tensors T1, T2) is adjusted via a tensor decomposition. The tensor decomposition includes or involves tensor amplification, thereby generating a set of tensor factors that amplify low rank structure, as described herein. In some cases, the implementation of the decomposition includes an act 314 in which a decomposition-based de-noising procedure is implemented, such as described in connection with FIG. 4. In some cases, a single decomposition is used for both de-noising and the dimensionality adjustment. Alternatively, such decomposition-based or other de-noising is implemented previously, such as in connection with obtaining tensor data in the act 302.

The dimensionality is adjusted so that the one or more patient-based tensors or the first and second class tensors have the same dimensionality. Once the tensors being compared have the same dimensionality, a similarity score may be computed, as described below. In some cases, adjusting the dimensionality includes, in an act 314 replacing a tensor factor generated via the tensor decomposition with a matrix that minimizes a distance between the tensors for which the first and second similarity scores are computed. For example, if the two tensors being compared have dimensions a×b×c and a×d×c, the decomposition of the first tensor is found for a suitably chosen rank r. The resulting tensor factor matrices A and C generated as described herein may then be combined with another tensor factor D to define a tensor decomposition [A, D, C]. The matrix D may then be found that minimizes the distance between the tensor a×d×c and [A, D, C]. Now the other tensor a×d×c and [A, D, C] have the same dimensions.

In an act 316, first and second similarity scores are computed for first and second tensor pairings of the one or more patient-based tensors relative to the first and second patient classes, respectively. For instance, the first pairing may be either the patient tensor P and the class tensor T1, or the tensor Q1 and the class tensor T1, with one of the tensors in the pairing having a dimensionality adjustment as described above. The second pairing is then either the patient tensor P and the class tensor T2, or the tensor Q2 and the class tensor T2, again with one of the tensors in the pairing having a dimensionality adjustment as described above.

The similarity scores may be computed in acts 318, 320 by determining a normalized inner product of the tensors for which the first and second similarity scores are computed. The inner product may be computed because the tensors in each pairing have the same dimensionality. Alternatively, computing the first and second similarity scores includes an act 322 implementing a CP decomposition procedure on the tensors for which the first and second similarity scores are computed.

The class (or corresponding condition) is then selected in an act 324 for the assessment based on the similarity scores. In the two class example described above, one of the first patient class and the second patient class is selected based on the computed first and second similarity scores. For instance, selecting the first patient class or the second patient class may include an act 326 in which it is determined which one of the first patient class and the second patient class has a higher similarity score. Output data indicative of the assessment corresponding with the selected class may then be provided in an act 328.

The order in which the acts of the method 300 are implemented may differ from the example shown in FIG. 3, and/or the method 300 may include additional, fewer or alternative acts. For instance, the method 300 may include multiple acts directed to obtaining the new patient tensor and/or the class tensors.

Figure 4:
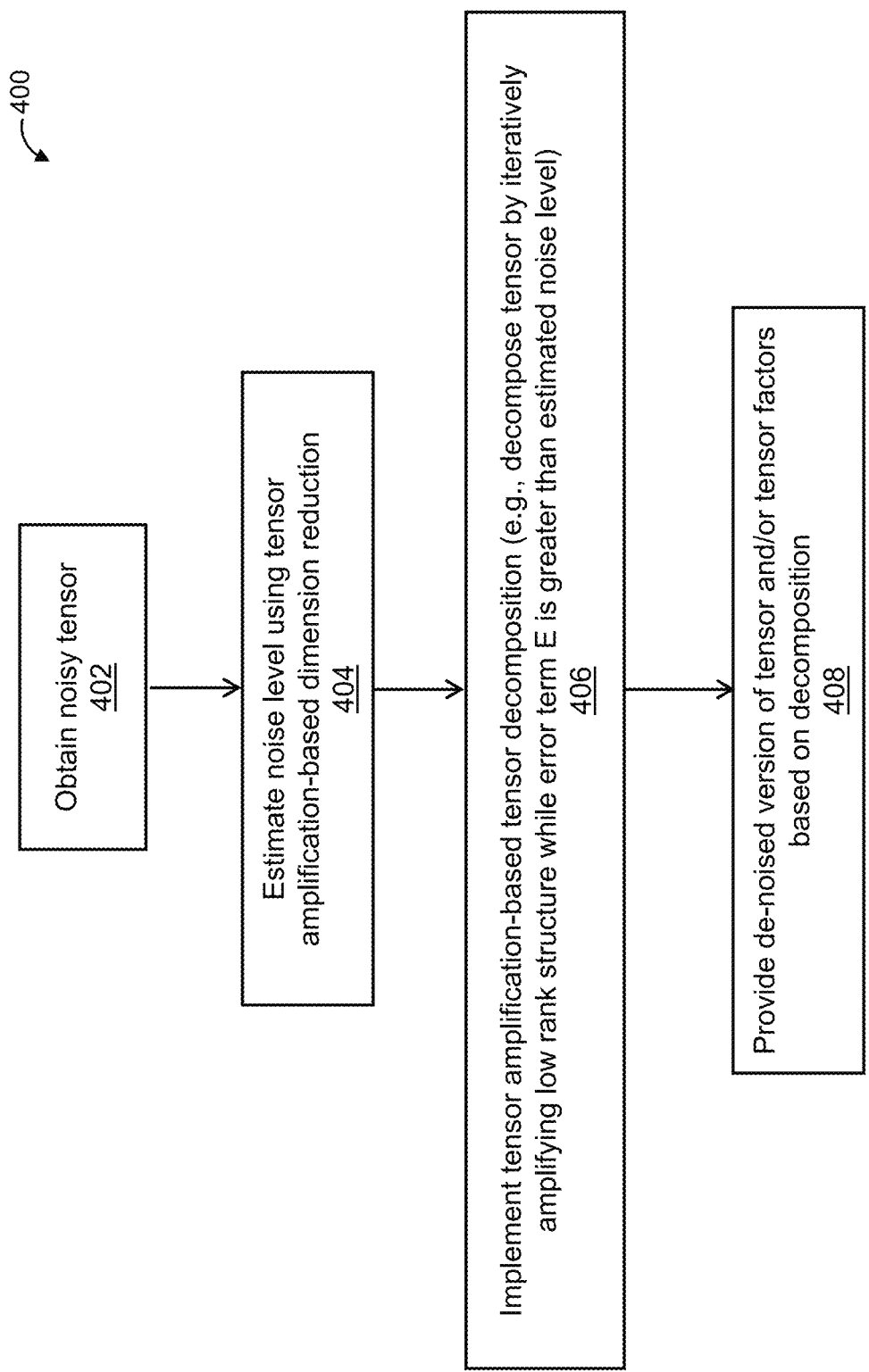
FIG. 4 depicts a flow diagram of a method of de-noising tensor data using tensor amplification-based decomposition in accordance with one example.

FIG. 4 depicts a method 400 of de-noising tensor data in accordance with another example. The method 400 may be used in conjunction with, e.g., as part of, any one of the medical condition assessment methods described herein, or another method. The method 400 may be implemented by any one or more of the systems or processors described herein, and/or another system or processor. The method 400 relies upon a tensor amplification-based decomposition.

The method 400 may begin, in an act 402, in which the tensor to be de-noised is obtained. The tensor data may be received, accessed, or obtained in another manner. In some cases, data indicative of the tensor is obtained. Obtaining the tensor may thus include forming the tensor from raw or other original data. In other cases, the tensor itself is directly received, accessed, or otherwise obtained.

In an act 402, a noise level of the tensor data is estimated using tensor amplification-based dimension reduction in accordance with the techniques described herein. For instance, the tensor amplification-based dimension reduction may include, as described herein, generating a set of tensor factors, each of which is indicative of a decomposition of the tensor data being de-noised. The tensor amplification-based dimension reduction obtains the reduced tensor T along with the error term E. The L2 norm (also called the Frobenius norm in the matrix/tensor context) of the error term E, denoted $\|E\|$, may then be used as an estimate for the level of noise in the original tensor. This estimate of the noise level may become the epsilon used in the tensor decomposition algorithm described above. Other techniques for estimating the noise level may be used in combination with the tensor amplification-based dimension reduction.

A decomposition is then implemented in an act 406 by iteratively amplifying low rank structure of the tensor data while an error term of the decomposition is greater than the estimated noise level. The error term of the decomposition may correspond with the term E in the decomposition example described above.

An output of the method 400 is provided in an act 408 when the error term is equal to or less than the estimated noise level. In some cases, tensor factors of the decomposition are provided. Alternatively or additionally, a de-noised version of the tensor data based on the tensor factors is provided.

Figure 5:
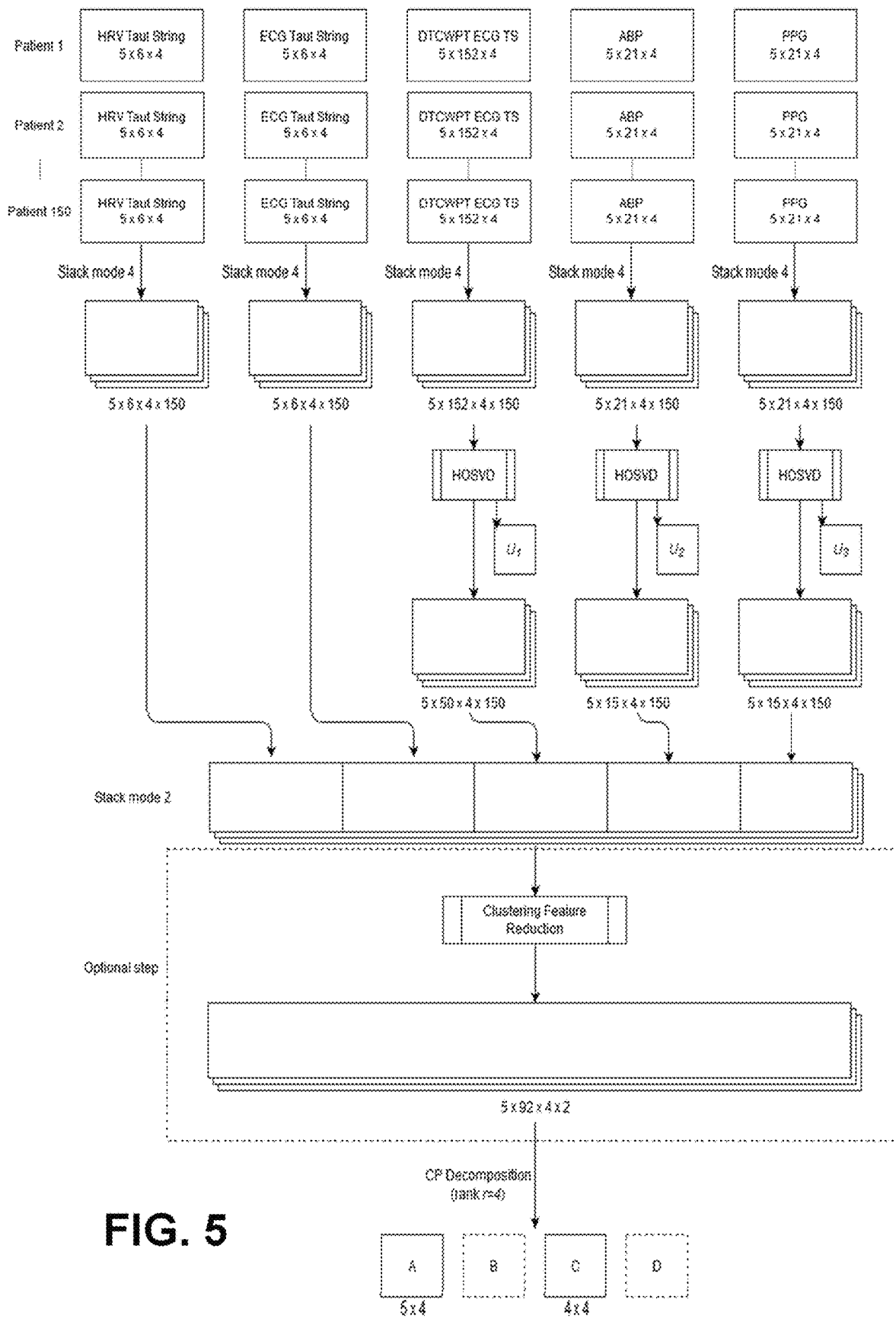
FIG. 5 depicts an example implementation of a method involving tensor amplification-based decomposition for feature reduction of training tensor data for a plurality of physiological tests.
Figure 6:
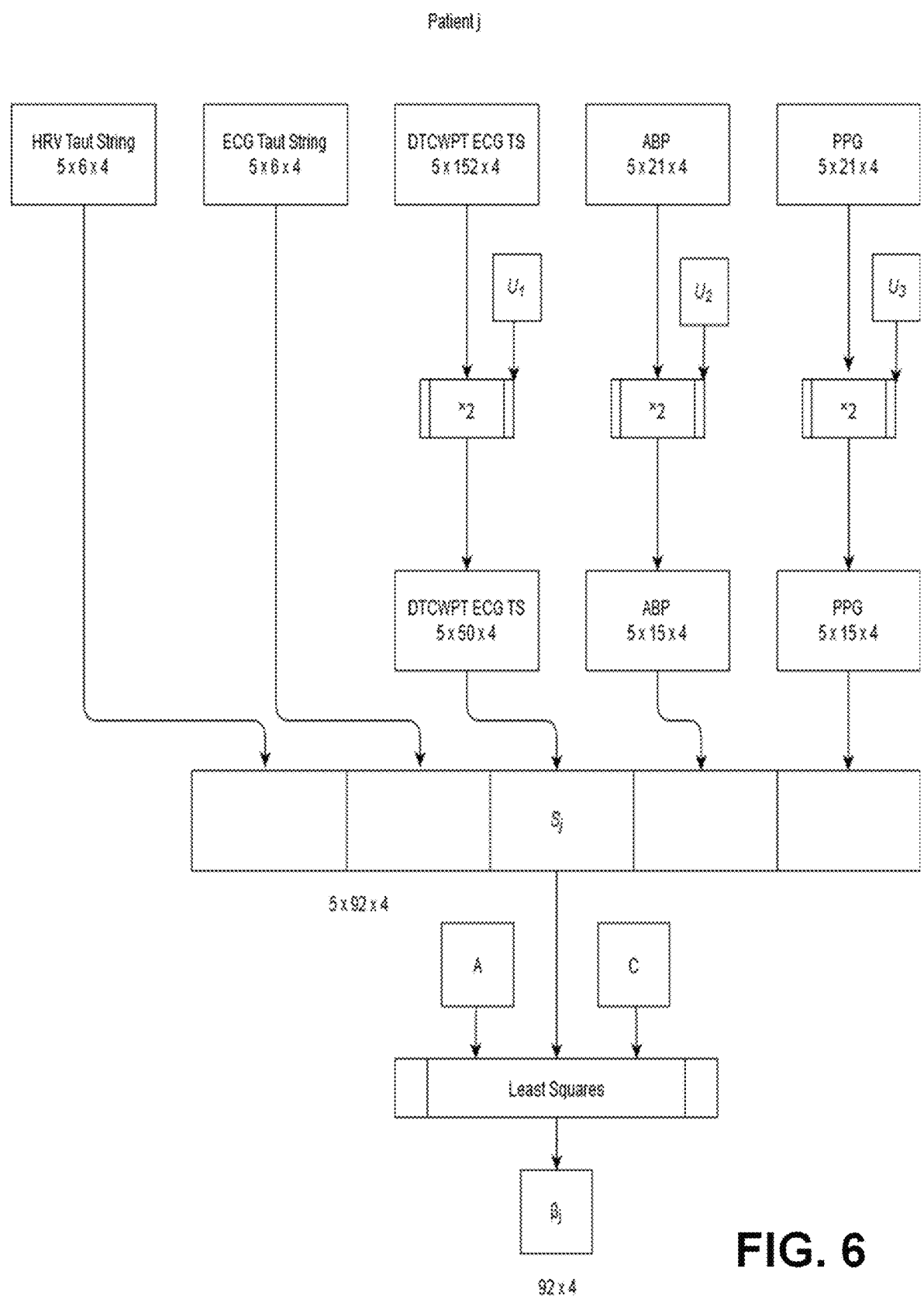
FIG. 6 depicts an example implementation of a method involving tensor amplification-based feature extraction from patient tensor data using the results of the decomposition of FIG. 5.

FIGS. 5 and 6 are directed to an example in which the tensor amplification-based decomposition techniques described herein are used for feature reduction in connection with a machine learning classifier-based assessment. In this example, the assessment relates to predicting whether a new patient will experience complications following cardiac surgery. Other types of assessments may be made, including, for instance, predictions of other types of post-surgery medical conditions. The feature reduction allows disparate sources of continuous and non-continuous patient data to be analyzed in order to understand and predict potential complications and/or recovery trends for the patients following surgery.

In this example, the underlying data includes electrocardiogramaignals that were processed to extract predictive features. Corresponding signal segments and features are also extracted from ABP signals. Photoplethysmography (PPG) signals are captured by pulse oximeters. The date and time of adverse events may be identified and analyzed for each patient who experienced complications during recovery. For patients who never experienced any adverse events, a random time during their observation period may be chosen as the fiducial time point. Multiple fiducial time points may be extracted for some of these patients. The fiducial time points may be alternatively or additionally chosen by making use of a uniform probability distribution. This approach allows the full spectrum of the recovery period to be captured in the analysis. In one example, a 12-minute window immediately preceding a fiducial time point is identified for each sample. This 12-minute window includes a 3-minute gap occurring immediately before the fiducial time-point, plus a 9-minute window for analyzing the signal data, e.g. the ECG, ABP, and PPG data. The physiological signal data during the 3-minute gap may not be used for analysis.

One example of the extraction of features from the ECG signals is now described. The ECG segments from the 9-minute analysis window are divided into four sub-windows of approximately 2.3 minutes. The signal within each of these 2.3-minute sub-windows is bandpass filtered with a 2nd order Butterworth filter to remove artifacts that commonly arise in these waveforms. The cutoff frequencies of this filter may be 0.5 and 40 Hz, for example. A peak detection algorithm is used to identify the R-peaks within each ECG. From the sequence of R-peaks, a Heart-Rate-Variability (HRV) sequence is generated. Taut String Estimation is applied to the HRV sequence. Morphological and statistical predictive features may then be extracted from each sub-window. These include the number of line segments per heartbeat, number of inflection segments per heartbeat, total variation of the noise per heartbeat, total variation of de-noised signal per heartbeat, power of the HRV noise, and power of the de-noised HRV. Five values of the above-referenced noise level parameter (delta) were utilized in Taut String Estimation of the HRV signal. These values are 0.001, 0.0258, 0.0505, 0.0753, and 0.100.

Taut String Estimation is also applied to the filtered ECG signal. Morphological and statistical predictive features are extracted from the resulting Taut String signal estimate of the electrocardiogram. These morphological and statistical features are calculated in the same manner as they were for the aforementioned Taut String Estimate of the HRV signal. Five values of the delta noise level parameter were utilized in Taut String Estimation of the ECG signal. These values are 0.0100, 0.1575, 0.3050, 0.4525, and 0.6000.

The Dual-Tree Complex Wavelet Packet Transform (DTCWPT) is applied to the aforementioned Taut String Estimate of the filtered ECG signal. The decomposition level, L, of the DTCWPT was set at 2. Predictive features are then extracted from each set of the eight sets of coefficients produced in the DTCWPT signal decomposition. These features include Shannon entropy, logarithm of the energy, power, mean coefficient value, maximum coefficient value, minimum coefficient value, standard deviation, the range of coefficient values, kurtosis, skewness, etc. For each value of delta, 152 features were extracted within a given sub-window. In total, there were 3,040 wavelet-based features (i.e., 3,040=152 features per delta*5 deltas per window*4 windows).

One example of the extraction of features from the ABP signals is now described. ABP signals occurring during the 9-minute analysis window are divided into four sub-windows of approximately 2.3 minutes. The arterial signal within each of these 2.3-minute sub-windows is band-pass filtered with a 3rd order Butterworth filter to remove artifacts. The cutoff frequencies of this filter may be 1.25 and 25 Hertz, for example. A peak detection algorithm is used to identify the systolic and diastolic peaks within each cycle of the signal. From these two peaks, the following metrics are calculated: mean, median, and standard deviation of the time interval between consecutive systolic peaks; mean, median, and standard deviation of the time interval adjacent systolic and diastolic peaks; mean, median, and standard deviation of the relative amplitude between consecutive systolic peaks; mean, median, and standard deviation of the relative amplitude between adjacent systolic and diastolic peaks; the total number of peaks. In total, there are 420 features per patient observation (i.e., 21 features per delta*5 deltas per window*4 windows).

One example of the extraction of features from the PPG signals is now described. PPG signals occurring during the 9-minute analysis window are divided into four sub-windows of approximately 2.3 minutes. The PPG signal within each of these 2.3-minute sub-windows is band-pass filtered with a 3rd order Butterworth filter to remove artifacts. The cutoff frequencies of this filter may be 1.75 and 10 Hertz, for example. The feature extraction process for PPG signals may be identical to the aforementioned process for ABP signals. Just as with the ABP signals, this process produces 420 features per patient observation.

Patient electronic health record (EHR) data is also incorporated into the tensor data. Such data may include patient demographics such as age and race, 30 Elixhauser comorbidities, lab results, administered medications, and respiratory support. The comorbidities are binary values that include a variety of clinically relevant diagnoses such as Obesity, Diabetes, Alcohol Abuse, Chronic Pulmonary Disease, and Drug Abuse, among others. Additional, fewer, or alternative EHR data may be obtained. For instance, lab results of various blood tests performed throughout a patient's stay may be used, including tests related to hematology, metabolites, kidney function, immune function, and coagulation, among others. Reference ranges may be used to encode the lab result values, e.g., as low, normal, or high. Medications for feature extraction may include those administered during the course of a patient's stay.

Features regarding respiratory support may also be included. For instance, the Fraction of Inspired Oxygen ($FiO_2$) as the supplemental oxygen provided for a patient up to a maximum of 100% (pure oxygen). Positive end-expiratory pressure (PEEP) settings for a patient receiving some form of mechanical ventilation that include pressure support may be included. If a patient isn't mechanically ventilated, the PEEP setting is 0. Also included is the patient's intubation status, i.e., whether or not they are receiving invasive mechanical ventilation. Whether or not a patient was re-intubated during each day of their stay may also be included as a feature. This is encoded as a) unknown, b) hasn't been re-intubated, or c) re-intubated.

With reference now to FIG. 5, all told, feature extraction yields 4, 120 features from the ECG, ABP, and PPG waveforms, along with 320 features from the EHR data. Rather than treating each set of waveform features as a one-dimensional feature vector, using the tensor amplification-based decomposition of the disclosed methods and systems, the natural tensor structure of these features to analyze the relationship between the signals and their attendant features, while simultaneously reducing the total number of features.

As shown in FIG. 5, the extracted waveform features for each patient are in 5 groups, namely 6 HRV Taut String features, 6 ECG Taut String features, 152 ECG wavelet features, 21 ABP features, and 21 PPG features. Each feature is measured for 4 distinct time sub-windows, and at 5 different values of delta. The 6 HRV Taut String features for each of the 5 values of delta and for each of the 4 windows gives a 5×6×4 tensor. Similarly, a 5×6×4 tensor of ECG Taut String features, a 5×152×4 tensor of ECG wavelet features, a 5×21×4 tensor of ABP features, and a 5×21×4 tensor of PPG features, are provided.

Using this data, a sequence of tensor analysis methods is implemented to determine the underlying structure within these tensors, after which a reduced set of features is extracted. The structure of the tensor data is determined by analyzing the tensor data for a training set. An example training set involving 150 patients is shown in FIG. 5. The HRV Taut String feature tensors of all 150 training patients are stacked in the fourth mode to create a 4-way tensor of size 5×6×4×150. The same stacking is done for the other groups of features. Some of the groups may have too many features to make tensor decomposition feasible. Thus, Higher Order Singular Value Decomposition (HOSVD) procedure may be used to reduce the number of features in those groups. For example, the a 5×152×4×150 tensor of ECG wavelet features is reduced to a 5×50×4×150 tensor. The HOSVD procedure may also give a matrix $U_1$ as output that gives the transformation from the 152-dimensional space to the 50-dimensional space. This process is repeated for the ABP and PPG features, which result in tensors of size 5×15×4×150 and transformation matrices $U_2$ and $U_3$. The 4-way tensors for each of the feature groups are stacked in mode 2 to obtain a 5×92×4×150 tensor T. Thus, after these dimension reductions, there are 6+6+50+15+15=92 features.

To explore whether or not the tensor structure for positive and negative patients in our cohort differs, the structure learning process includes an optional clustering step. In this step, the dimension in the fourth mode is reduced to obtain a 5×92×4×2 tensor as follows. Suppose there are x positive cases. The positive cases are clustered together to form a 5×92×4×x tensor and HOSVD decomposition is used to reduce the cluster to a tensor of size 5×92×4×1. The negative cases are clustered together to form a 5×92×4×(150 −x) tensor and HOSVD decomposition is again used to obtain another size 5×92×4×1 tensor. Finally, the two tensors of size 5×92×4×1 are stacked to get a size 5×92×4×2 tensor. We replace the tensor T by the reduced tensor of size 5×92×4×2. When this optional step is performed, the resultant features are referred to as "Clustered"; if this step is skipped the features are referred to as "Non-Clustered".

In the final step in determining the tensor structure, the tensor amplification-based decomposition procedure is implemented with rank r on the tensor T, which now may have size 5×92×4×150 or 5×92×4×2, depending whether the cluster dimension reduction step was performed. The output of the decomposition is as follows:

$$T = \Sigma_{i=1}^{r} a_i \otimes b_i \otimes c_i \otimes d\_i$$

As described above, the vectors $a_1, a_2, \ldots, a_r$ are grouped together to generate a matrix A. In this case, the matrix A has a size 5 r. Similar matrices (e.g., B, C, D) may be generated from the other sets of tensor factors. The matrix B has a size 92×r in this case. In this example, the matrices B and D are discarded, and the matrices A and C are used as transformation factors. The classifier is then trained using the factor matrices A and C on the training data to create feature vectors for the training patient data.

Turning to FIG. 6, the transformation matrices may be used to extract features for each training patient data set (i.e., to be used in training the classifier) and a new patient data set to be assessed. For each patient (e.g., patient j), the matrices $U_1$, $U_2$, and $U_3$ are used to reduce the number of wavelet, ABP, and PPG features. The dimension-reduced tensors for all feature groups are stacked together to construct a 5×92×4 tensor $S_j$. The matrices A and C provide the vectors $a_1, a_2, \ldots, a_r$ and $c_1, c_2, \ldots, c_r$. Using those vectors, a least squares problem is solved to determine the vector $b_1$, $b_2, \ldots, b_r$ that minimizes the following expression:

$$\|S_j - \Sigma_{i=1}^{r} a_i \otimes b_i \otimes c_i\|.$$

In this case, the resulting feature vector $b_1, b_2, \ldots, b_r$ is of length 92*4 or 368. The new physiological feature vectors of length 368 for each patient (e.g., training patient) are combined with the Electronic Health Records (EHR) features (e.g., 320 features) and then used as input into a machine learning classifier, such as a classifier based on a Random Forest model or a Non-Convex Kernels method. Other types of machine learning classifiers may be used.

The tensor-based feature reduction methods described above transform the 4, 120 signal-based features to a much smaller set of 368 values. This is a 91% reduction in the number of signal-based features. When the 320 features from the EHR data are combined with 368 tensor-derived features, the total number of features is reduced to 688. This is an 85% reduction from the original value of 4,440. As a result of this significant reduction, the training time for the machine learning classifiers is reduced considerably. The feature reduction also leads to improvements in classifier performance. In these and other ways, the tensor-based reduction techniques of the disclosed methods and systems provide useful advantages for predictive modeling with large data sets.

Figure 7:
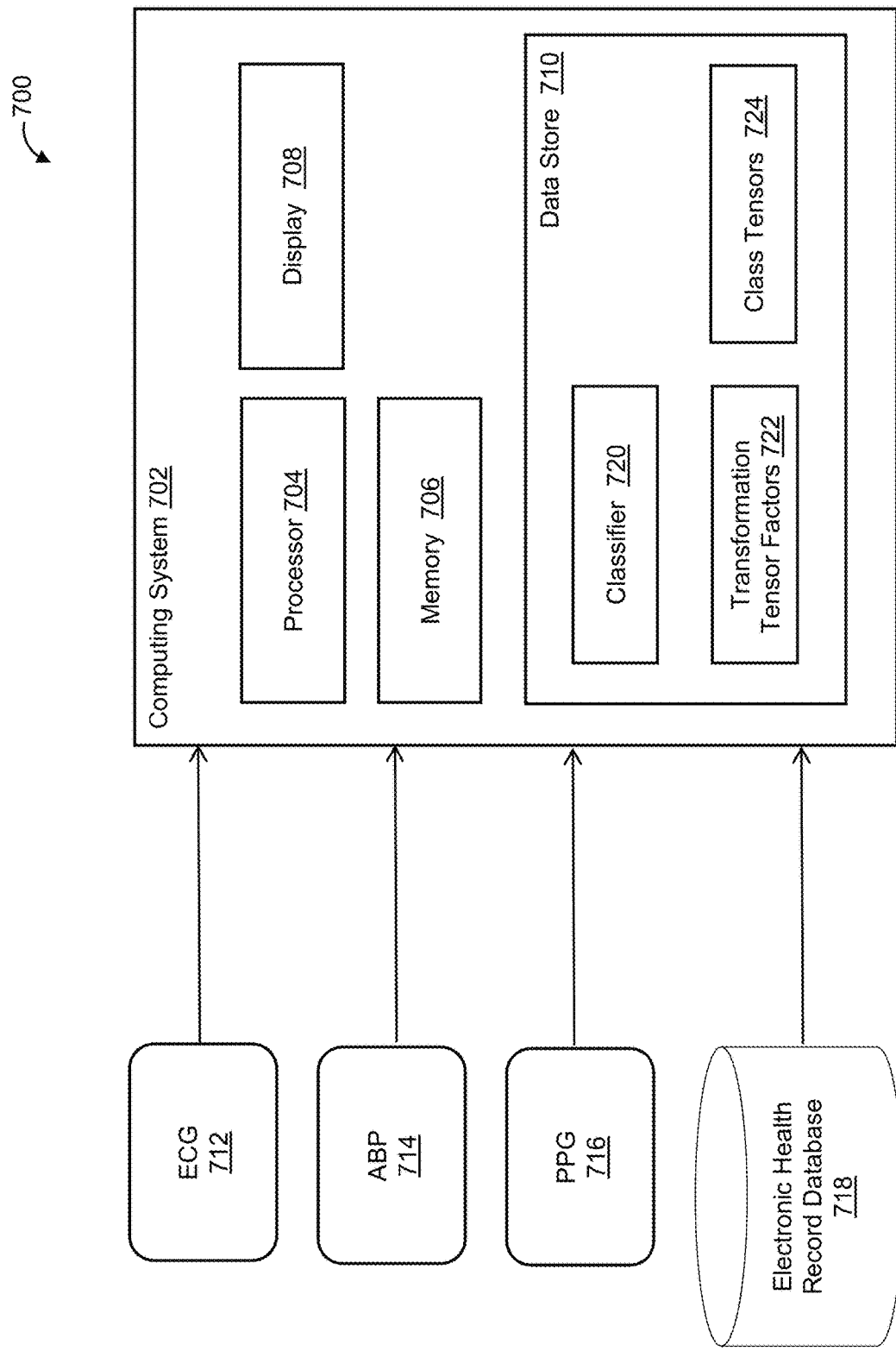
FIG. 7 is a schematic view of a system for implementing any of the methods of FIGS. 1-6.

FIG. 7 depicts a system 700 that may be used to implement one of the above-described methods. For example, the system 700 may be used to implement the medical condition assessment method 200 of FIG. 2. Alternatively or additionally, the system 700 may be used to implement the feature reduction techniques described above in connection with the examples of FIGS. 5 and 6.

The system 700 includes a computing system 702 having a processor 704, a memory 706, a display 708, and a data store 710. Instructions stored in the memory 706 are executed by the processor 704 to implement one or more of the acts of the above-described methods. The output of the methods, such as a medical condition assessment may be provided via the display 708. The computing system 702 may be integrated with a data collection device or system, such as an imaging system, to any desired extent.

The computing system 702 may be coupled to one or more components to obtain patient data. In this example, the computing system 702 receives signal data from an ECG system 712, an ABP system 714, and a PPG system 716. Additional, fewer, or alternative signal data systems may be included. For instance, one or more imaging systems may be included. The computing system 702 may also receive EHR data from a database 718. Alternatively or additionally, some or all of the signal or other patient data is stored in the data store 710 for access by the processor 704.

In the example of FIG. 7, data indicative of a machine learning classifier 720 is stored in the data store 710. Other types of data that may be generated and later used by the processor 704 may also be stored in the data store 710, including, for instance, data transformation tensor factors 722 (e.g., for feature reduction) and class tensor data 724 (e.g., for similarity score-based assessments).

The processor 704 may include any number of processors, processing units, or other processing devices or systems. In some cases, the processor 704 is or includes a digital signal processor, a general processor, an application specific integrated circuit, a field programmable gate array, a control processor, digital circuitry, analog circuitry, a graphics processing unit, combinations thereof or other now known or later developed device for implementing calculations, algorithms, programming or other functions.

The memory 706 may include any number of memory units, devices or systems. In some cases, the memory 706 is or includes random access memory, removable media (e.g. compact disc), a hard drive, a database, or other memory device for storing instructions, patient data, and/or other data.

The data store 710 may include any number of data storage units, devices or systems.

The present disclosure has been described with reference to specific examples that are intended to be illustrative only and not to be limiting of the disclosure. Changes, additions and/or deletions may be made to the examples without departing from the spirit and scope of the disclosure.

The foregoing description is given for clearness of understanding only, and no unnecessary limitations should be understood therefrom.

What is claimed is:

1. A method of generating an assessment of medical condition for a patient, the method comprising:
   obtaining, by a processor, a patient data tensor indicative of a plurality of tests conducted on the patient;
   obtaining, by the processor, a set of tensor factors, each tensor factor of the set of tensor factors being indicative of a decomposition of training tensor data for the plurality of tests, the decomposition amplifying low rank structure of the training tensor data;
   determining, by the processor, a patient tensor factor for the patient based on the obtained patient data tensor and the obtained set of tensor factors;
   applying, by the processor, the determined patient tensor factor to a classifier such that the determined tensor factor establishes a feature vector for the patient, the classifier being configured to process the feature vector to generate the assessment; and
   providing, by the processor, output data indicative of the assessment.

2. The method of claim 1, wherein the set of tensor factors comprises a tensor factor indicative of a correlation of the decomposition to multiple predetermined values of a noise level parameter.

3. The method of claim 1, wherein the set of tensor factors comprises a tensor factor indicative of a correlation of the decomposition to timing windows for the plurality of tests.

4. The method of claim 1, wherein determining the patient tensor factor comprises solving a least squares problem to minimize a difference between the patient data tensor and a tensor product of the obtained tensor factors and the patient tensor factor.

5. The method of claim 1, further comprising forming the feature vector for the patient by combining the determined patient tensor factor with electronic health record data for the patient.

6. The method of claim 1, wherein the obtained set of tensor factors is indicative of training data processed via a procedure in which the training data is clustered in accordance with presence of the medical condition.

7. The method of claim 1, wherein the plurality of tests comprises an electrocardiogram (ECG) test, a blood pressure test, and a photoplethysmography (PPG) test conducted during a time period window.

8. The method of claim 1, wherein the low rank structure comprises a plurality of rank 1 tensors.

9. A method of generating an assessment of medical condition for a patient, the method comprising:
   obtaining, by a processor, tensor data comprising one or more patient-based tensors for patient data indicative of a plurality of tests conducted on the patient and first and second class tensors for first and second patient classes with and without the medical condition, respectively;
   adjusting, by the processor, dimensionality of either the one or more patient-based tensors or the first and second class tensors via a tensor decomposition so that the one or more patient-based tensors or the first and second class tensors have a same dimensionality, the tensor decomposition generating a set of tensor factors that amplify low rank structure;
   computing, by the processor, first and second similarity scores for first and second tensor pairings of the one or more patient-based tensors relative to the first and second patient classes, respectively;
   selecting, by the processor, the first patient class or the second patient class for the assessment based on the computed first and second similarity scores; and
   providing, by the processor, output data indicative of the assessment.

10. The method of claim 9, wherein adjusting the dimensionality comprises replacing a tensor factor generated via the tensor decomposition with a matrix that minimizes a distance between tensors for which the first and second similarity scores are computed.

11. The method of claim 9, wherein obtaining the tensor data comprises stacking the patient data onto the first and second class tensors to create first and second patient-based tensors.

12. The method of claim 9, wherein computing the first and second similarity scores further comprises determining a normalized inner product of tensors for which the first and second similarity scores are computed.

13. The method of claim 9, wherein computing the first and second similarity scores further comprises implementing a canonical polyadic (CP) decomposition procedure on tensors for which the first and second similarity scores are computed.

14. The method of claim 9, wherein selecting the first patient class or the second patient class comprises determining which of the first patient class and the second patient class has a higher similarity score.

15. The method of claim 9, wherein the low rank structure comprises a plurality of rank 1 tensors.

16. A method of de-noising tensor data in preparation for a medical condition assessment, the method comprising:
   obtaining, by a processor, the tensor data;
   estimating, by the processor, a noise level of the tensor data using tensor amplification-based dimension reduction;
   implementing, by the processor, a decomposition by iteratively amplifying low rank structure of the tensor data while an error term of the decomposition is greater than the estimated noise level; and
   providing, by the processor, tensor factors of the decomposition when the error term is equal to or less than the estimated noise level, or a de-noised version of the tensor data based on the tensor factors.

17. The method of claim 16, wherein implementing the decomposition comprises implementing a tensor amplification-based tensor decomposition.

18. The method of claim 16, wherein the low rank structure comprises a plurality of rank 1 tensors.

19. The method of claim 16, wherein estimating the noise level using tensor amplification-based dimension reduction comprises generating a set of tensor factors, each tensor factor of the set of tensor factors being indicative of a decomposition of the tensor data.

20. The method of claim 16, wherein the tensor data is indicative of physiological data.

* * * * *